(12) United States Patent
Lewin Jessen et al.

(10) Patent No.: US 10,512,750 B1
(45) Date of Patent: Dec. 24, 2019

(54) BONE CONDUCTION SPEAKER PATCH

(71) Applicant: X Development LLC, Mountain View, CA (US)

(72) Inventors: Johan Ulrich Lewin Jessen, Mountain View, CA (US); Matthew David Day, Oakland, CA (US); Preeti Murali Talwai, El Dorado Hills, CA (US)

(73) Assignee: X Development LLC, Mountain View, CA (US)

( * ) Notice: Subject to any disclaimer, the term of this patent is extended or adjusted under 35 U.S.C. 154(b) by 161 days.

(21) Appl. No.: 15/392,825

(22) Filed: Dec. 28, 2016

(51) Int. Cl.
*A61M 21/00* (2006.01)
*H04R 25/00* (2006.01)

(52) U.S. Cl.
CPC .............. *A61M 21/00* (2013.01); *H04R 25/60* (2013.01); *A61M 2021/0022* (2013.01); *A61M 2021/0066* (2013.01); *A61M 2205/3303* (2013.01); *A61M 2210/06* (2013.01); *A61M 2230/005* (2013.01); *A61M 2230/08* (2013.01); *A61M 2230/20* (2013.01); *A61M 2230/201* (2013.01); *A61M 2230/50* (2013.01); *A61M 2230/63* (2013.01); *H04R 2460/13* (2013.01)

(58) Field of Classification Search
CPC ...................... A61M 2021/0027; A61M 21/00
See application file for complete search history.

(56) References Cited

U.S. PATENT DOCUMENTS

| | | | |
|---|---|---|---|
| 4,830,014 A | 5/1989 | Goodman | |
| 7,477,753 B2 | 1/2009 | Buckley | |
| 8,795,172 B2 | 8/2014 | Abolfathi et al. | |
| 9,031,274 B2 | 5/2015 | Kasic | |
| 9,439,599 B2 | 9/2016 | Thompson | |
| 9,682,001 B1* | 6/2017 | Simon | A61B 5/486 |
| 2002/0183014 A1* | 12/2002 | Takeda | H04R 1/14 455/73 |
| 2004/0222638 A1 | 11/2004 | Bednyak | |
| 2006/0252979 A1 | 11/2006 | Vesely | |

(Continued)

OTHER PUBLICATIONS

Final Office Action issued in U.S. Appl. No. 15/392,836, dated Aug. 3, 2018, 19 pages.

(Continued)

*Primary Examiner* — Kaylee R Wilson
(74) *Attorney, Agent, or Firm* — Fish & Richardson P.C.

(57) ABSTRACT

A bone conduction device includes: an enclosure; and an adhesive applied to a surface of the enclosure, in which the enclosure includes: a bone conduction transducer configured to cause the enclosure to vibrate; at least one sensor configured to sense a non-audible input from a region of the user's skin to which the adhesive adheres and produce a sensor output signal in response to sensing the non-audible input, the sensor output signal being indicative of a current state of the user; and a transceiver coupled to the bone conduction transducer and to the at least one sensor, in which the transceiver is configured to a) receive the output signal from the sensor and transmit the output signal to a remote processor and b) in response to transmitting the output signal, receive the bone-conduction control signal from the remote processor and transmit the bone-conduction control signal to the bone conduction transducer.

15 Claims, 4 Drawing Sheets

(56) References Cited

U.S. PATENT DOCUMENTS

| | | | |
|---|---|---|---|
| 2008/0004679 A1* | 1/2008 | Naghavi | A61N 2/002 |
| | | | 607/108 |
| 2011/0077056 A1* | 3/2011 | Park | H04W 52/0254 |
| | | | 455/569.1 |
| 2011/0125063 A1 | 5/2011 | Shalon | |
| 2015/0073309 A1 | 3/2015 | Pracar | |
| 2015/0157255 A1 | 6/2015 | Nduka | |
| 2015/0268673 A1* | 9/2015 | Farzbod | G02B 27/0176 |
| | | | 700/280 |
| 2016/0249141 A1 | 8/2016 | Verdooner et al. | |
| 2016/0267310 A1* | 9/2016 | AlNasser | G06K 7/10009 |
| 2016/0296799 A1 | 10/2016 | Macagnano | |
| 2016/0361015 A1* | 12/2016 | Wang | A61B 5/6832 |
| 2017/0039045 A1 | 2/2017 | Abrahami | |
| 2017/0055896 A1 | 3/2017 | Al-Ali | |
| 2017/0156623 A1 | 6/2017 | Chu | |
| 2017/0309152 A1 | 10/2017 | Dinkins | |
| 2017/0323068 A1* | 11/2017 | Dintenfass | G06Q 40/06 |
| 2018/0014741 A1 | 1/2018 | Chou | |

OTHER PUBLICATIONS

'jiwonjun.com' [online] "Bone Conducting Speaker Sticker (BCSS)," [Retrieved on Jan. 23, 2017] Retrieved from Internet: URL<http://jiwonjun.com/Bone-Conductive-Speaker-Sticker> 4 pages.

Non-Final Office Action issued in U.S. Appl. No. 15/392,836, dated Jan. 31, 2018, 14 pages.

Notice of Allowance issued in U.S. Appl. No. 15/392,836, dated Oct. 24, 2018, 10 pages.

\* cited by examiner

BONE CONDUCTION SPEAKER PATCH

BACKGROUND

Bone conduction is the conduction of sound to the inner ear through the bones of a user.

SUMMARY

The present disclosure relates to a bone conductor speaker patch.

In general, in some aspects, the subject matter of the present disclosure may cover bone conduction devices that include: an enclosure; and an adhesive applied to a surface of the enclosure, the adhesive being configured to be removably adhered to a user's skin, in which the enclosure includes: a bone conduction transducer configured to cause the enclosure to vibrate in response to receiving a bone-conduction control signal; at least one sensor configured to, during operation of the bone conduction device, sense a non-audible input from a region of the user's skin to which the adhesive adheres and produce a sensor output signal in response to sensing the non-audible input, the sensor output signal being indicative of a current state of the user; and a transceiver coupled to the bone conduction transducer and to the at least one sensor, in which the transceiver is configured to a) receive the output signal from the sensor and transmit the output signal to a remote processor and b) in response to transmitting the output signal, receive the bone-conduction control signal from the remote processor and transmit the bone-conduction control signal to the bone conduction transducer.

Implementations of the devices may include one or more of the following features. For example, in some implementations, the sensor includes accelerometer, a speedometer, a gyroscope, a galvanometer, a photodetector, a temperature sensor, a pulse oximetry sensor, a glucose monitor, and a pressure sensor.

In some implementations, the devices include an additional transducer, the additional transducer being configured to generate a non-audible sensation and direct the non-audible sensation to the region of the user's skin to which the adhesive adheres. The additional transducer may include a heating device or a cooling device.

In some implementations, the bone conduction device is configured to be activated upon the bone conduction device being exposed to a triggering event. The triggering event may include a change in pressure in an ambient environment to the bone conduction device. The triggering event may be indicative of the bone conduction device having been applied to the user's skin. The triggering event may include an activation control signal. The bone conduction device may be configured to deactivate upon being removed from the user's skin.

In some implementations, the bone conduction device is configured to authenticate the user upon being adhered to the user's skin. The bone conduction device may be configured to authenticate the user based on an analysis of a biometric measurement signal generated by the at least one sensor. The bone conduction device may include a local processor communicatively coupled to the at least one sensor and configured to receive and analyze the biometric measurement signal generated by the at least one sensor.

In some implementations, the bone conduction device is configured to authenticate multiple users based on multiple biometric measurement signals, respectively. Each biometric measurement signal of the multiple biometric measurement signals may be unique to a different user of the multiple users. The bone conduction device may include a local processor communicatively coupled to the at least one sensor, in which the local processor is configured to perform authentication upon being adhered to the user's skin.

In some implementations, the enclosure is flexible such that it is capable of conforming to a shape of the user's body upon being adhered to the user's skin.

In some implementations, the adhesive is an acrylic-based pressure sensitive adhesive.

In some implementations, the bone-conduction control signal is configured to cause the bone conduction transducer to generate an output to alter the state of the user or the user's perception of the state In general, in some aspects, the subject matter of the present disclosure may cover methods that include: detecting, with a sensor in a bone conduction device adhered to a user's skin, a non-audible input from a region of the user's skin to which the bone conduction device is adhered; generating, with the sensor, a measurement signal corresponding to the detected non-audible input; wirelessly transmitting the measurement signal to a processor remote to the bone conduction device; receiving, from the processor remote to the bone conducting device, a bone conduction transducer control signal; and passing the received bone conduction transducer control signal to a bone conduction transducer within the bone conduction device to cause the bone conduction transducer to generate a first output to alter the state of the user or the user's perception of the state.

Implementations of the methods may include one or more of the following features. For example, in some implementations, the methods include: receiving, from the processor remote to the bone conducting device, a second transducer control signal; and passing the second transducer control signal to a second transducer within the bone conduction device to cause the second transducer to generate a second output to alter the state of the user or the user's perception of the state.

In some implementations, the state of the user includes a physical and/or emotional state of the user.

In some implementations, the methods include: receiving, at the bone conduction device, a triggering event; and responsive to receiving the triggering event, activating or deactivating the bone conduction device.

One or more of the foregoing implementations may have various advantages. For example, in some implementations, the bone conduction device is capable of obtaining information about the state, emotion, current experience and/or mood of a user and, based on that information, generating a response that may modify or alter the user's perceived state, emotion, experience and/or mood. The response generated by the bone conduction device may improve a user's current experience to make the experience more enjoyable. Alternatively, the response generated by the bone conduction device may complement a user's experience to allow the user to become more immersed in their experience. Alternatively, the response generated by the bone conduction device may de-intensify the user's current experience, allowing the user to better focus on a task or perform a task with less anxiety.

The details of one or more embodiments are set forth in the accompanying drawings and the description below. Other features and advantages will be apparent from the description, the drawings, and the claims.

BRIEF DESCRIPTION OF THE DRAWINGS

Like reference symbols in the various drawings indicate like elements.

DETAILED DESCRIPTION

The present specification relates to a concealable bone conduction device that includes one or more sensors for receiving data from a user regarding a state/condition of the user and/or about an ambient environment in which the user is located. The present specification further relates to a bone conduction transducer that transmits vibrations to the user's bone in response to, and based on, the received inputs such that the user's perceived experience/state may be altered.

Figure 1A:
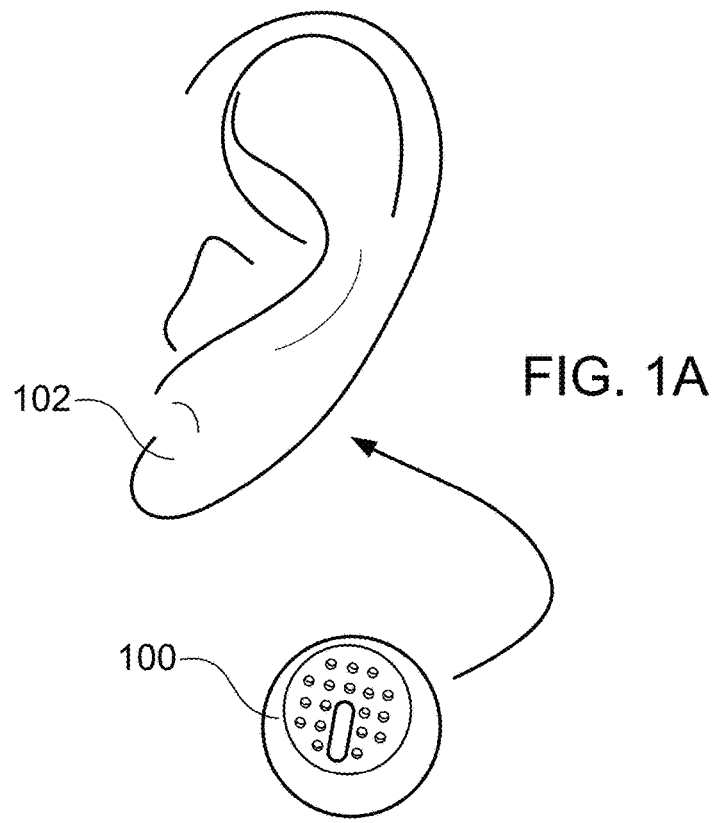
FIGS. 1A-1B are schematics illustrating an example bone conduction device as applied behind the ear of a user.
Figure 1B:
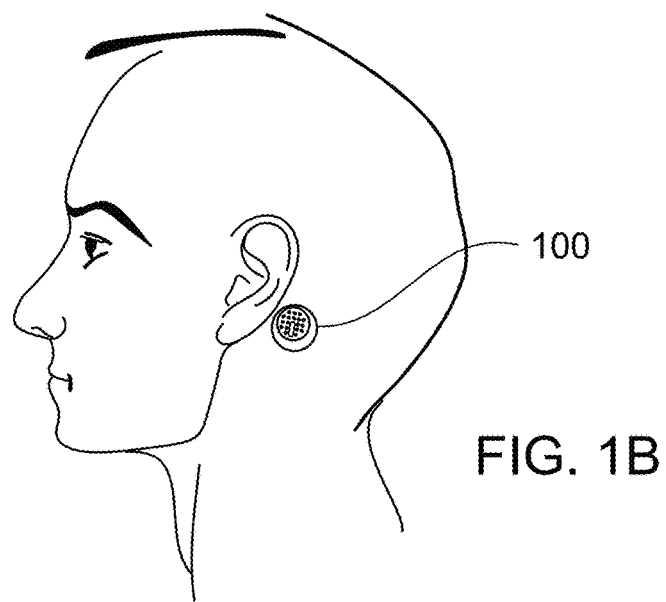

FIGS. 1A-1B are schematics illustrating an example bone conduction device 100 as applied behind the ear of a user. The bone conduction device 100 is shown in the example of FIGS. 1A-1B in the form of a patch that is placed behind a user's ear 102. By placing the bone conduction patch 100 behind the user's ear, this allows the bone conduction device 100 to be concealed from a casual observer. In some examples, the bone conduction device 100 also may be formed partly or wholly of material that is similar to, or matches, a user's skin tone and/or texture. As described herein, said material forming at least part of the bone conduction device 100 also may be flexible or malleable to conform to a user's skin topography. The bone conduction device 100 is capable of transmitting sound to the user by way of generating vibrations that, when the device 100 is placed against the user's skin, pass to the user's skull and from the skull to the user's auditory system. With the placement of the device 100, as shown in FIG. 1, the vibrations may be transmitted to the user's auditory system through, e.g., the user's mastoid bone. Though device 100 is illustrated in FIG. 1 as being placed behind a user's ear in order to generally conceal the device from observers facing the user, the device 100 may be placed against other areas of a user's body that are also capable of transmitting vibrations to the user's auditory system. For example, the device 100 may be placed against a different part of the mastoid bone, or a user's wrist, hand, or leg. Placing the device 100 further from the user's auditory system may, however, diminish the ability of the user to hear the sound from the vibrations due to a decrease in signal strength and/or an increase in noise. In such cases, the amplitude and/or frequency of the vibrations produced by the bone conduction device 100 may be adjusted to compensate for the increase in distance to the user's auditory system.

During operation of the device 100, one or more sensors in the device 100 may measure physical properties associated with the user's current state (e.g., emotional state, experience, or mood) and/or with the environment in which the user is located. For instance, the one or more sensors may generate a signal indicative of the user's pulse rate, the user's level of perspiration, the user's temperature, the user's voice, the user's acceleration, the user's velocity, the user's orientation, and odors from the user, among other physical properties and biometrics of the user. Alternatively, or in addition, the one or more sensors may generate a signal indicative of the temperature of the ambient environment, sounds from the ambient environment, and odors from the ambient environment, among other physical properties of the environment.

The signals generated from the one or more sensors may be transmitted from the bone conduction device to a remote device that analyzes the signals to determine a particular mood and/or emotional state of the user and, responsive to the received signals, sends one or more control signals back to the bone conduction device 100. The one or more control signals may cause the bone conduction device 100 to generate vibrations that are passed to the user's auditory system through bone conduction to alter the user's perceived mood, experience and/or emotional state. A user's emotional state may be understood as the user's state of mind deriving from the particular circumstances and environment the user is experiencing. An emotional state may include, e.g., anxiousness, fear, or calmness, among other emotional states.

As an example, in some implementations, the particular signals obtained by the one or more sensors of the bone conduction device may correlate with the user feeling anxious or afraid (e.g., a particular or threshold pulse rate, frequency and/or volume of voice, breathing rate). The control signals received by the device 100 may cause the device 100 to generate vibrations that, when received by the user's auditory system, allow the user to hear sounds associated with a calming effect (e.g., music, an augmented sound field such as the sound of birds singing, trees swaying, or ocean waves, or noise cancellation to reduce certain ambient noises such as traffic). Thus, the outputs of the bone conduction device may alter the user's experience and/or emotional state. In some implementations, the control signals cause the bone conduction device 100 to generate sounds based on the particular location of the user (e.g., whether the user is in a city, in a rural area, at street level, or in a high rise building.) In some implementations, the control signals cause the bone conduction device 100 to generate sounds based on the user's activity (e.g., whether biking, talking, running, or listening to music). The device 100 may include one or more additional transducers that also may alter the user's perceived state, experience and/or mood. For example, the one or more additional transducers may include a heating and/or cooling element. Such heating and/or cooling elements may, e.g., alter the user's physio-response such that the user feels hotter or colder. Such heating and/or cooling elements also may alter the user's perception of a physio-response such as making the user feel, e.g., lighter or heavier. In another example, the one or more additional transducers also may provide haptic or other stimulation to alter the user's perceived physio-response such that the user feels, e.g., hotter or colder, calmer or more alert, than the user actually is. Other modifications of the user's perceived state, experience and/or mood are also possible.

Figure 2:
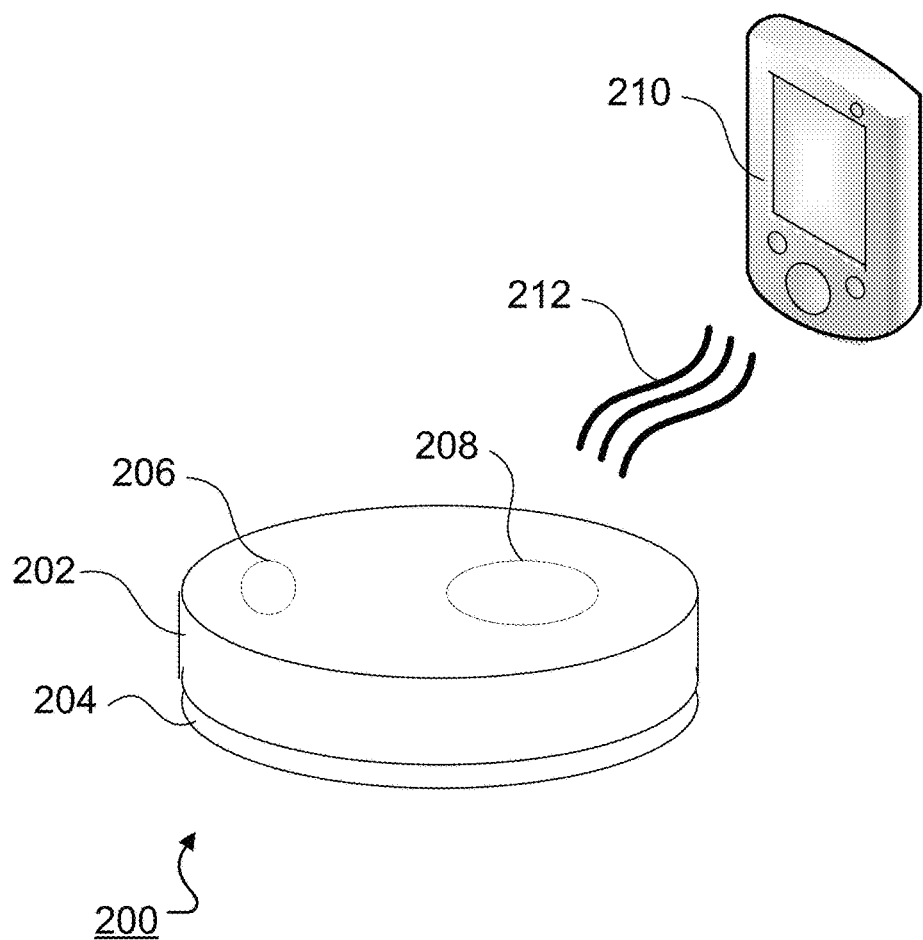
FIG. 2 is a schematic of an example bone conduction device according to the present disclosure.

FIG. 2 is a schematic of an example bone conduction device 200 according to the present disclosure. The device 200 is in the form of a patch that may be affixed to a user's body. The device 200 includes an enclosure 202 that contains a bone conduction transducer, among other components to be discussed in further detail. In some implementations, the enclosure is made of a rigid plastic. In other implementations, the enclosure 202 is made of a flexible material such that the enclosure 202 can easily conform to the shape of a portion of the user's body to which the device 200 attaches with little force and without cracking or breaking, but that is rigid enough to protect the internal components of the device. For instance, the enclosure may be made of a flexible plastic or of rubber. In such cases, it is advantageous to also position the electronic components contained within the enclosure 202 on a flexible board (e.g., a flexible printed circuit board having a flexible insulator such as polyimide, polyethylene napthalate, or polyethylene terephthalate) so that the probability of damage to the components during device flexure is reduced. The enclosure 202 is shown as being generally disc-shaped, but other shapes may be used instead. The enclosure 202 may be designed to be small relative to an average adult's head or ear so that it is easily concealable behind the ear. For example, the enclosure 202 may have a maximum average dimension (e.g., a maximum average diameter) greater than about 1 cm, but no more than about 2 cm, no more than about 3 cm, no more than about 4 cm, or no more than about 5 cm.

The device 200 further includes an adhesive 204 applied to a surface of the enclosure 202. In some implementations, the adhesive 204 covers an entire surface of the enclosure that faces the user. In some implementations, the adhesive 204 is applied in a pattern that covers less than an entire surface of the enclosure. For example, the adhesive 204 may be in the shape of a contiguous or noncontiguous ring, a series of concentric rings, a cross, or a periodic or random array of circles. Other patterns are possible as well. The adhesive 204 may include any adhesive suitable for adhering the enclosure 202 to a user's skin. For example, the adhesive 204 may include an acrylic-based pressure sensitive skin adhesive. The device 200 is applied to a user's body by placing the side of the enclosure having the adhesive 204 against the user's skin and applying pressure so that the enclosure 202 is retained in place. The adhesive 204 maintains the enclosure 202 against the user's skin so that the user can move around without the device 200 falling off. The adhesive 204 is designed to be removable by applying adequate force on the device 200 away from the user's skin. The adhesive 204 may be designed so that the device 200 can be repeatedly stuck and unstuck from the user's skin without needing to replace the adhesive 204. Alternatively, the adhesive 204 may be designed for one-time use. In some implementations, the adhesive 204 is removably secured to the enclosure 202. For example, the adhesive 204 may be a thin layer of polymer that can be peeled away from the enclosure surface. In some implementations, the adhesive 204 may be secured against the surface of the enclosure 202 using a retaining clip, screw, pin, or other securing mechanism. In some implementations, the adhesive 204 is transparent to visible and/or infrared light, such that light generated by sensor within the device 200 or light to be detected by a sensor within the device 200 may pass through the adhesive 204 without being substantially absorbed, reflected or refracted.

In some implementations, the enclosure 202 includes one or more openings or holes 206 on its surface. The openings or holes 206 may allow certain sensors within the enclosure 202 access to the environment to measure the property for which the sensors are designed. For example, in some implementations, the openings 206 may allow air from the ambient environment to enter into the enclosure 202 so that the air can be analyzed by a sensor configured to measure chemicals, such as odors or toxins. In another example, the openings 206 may allow secretions from the user (e.g., perspiration) to enter into the enclosure so that the secretions can be analyzed by the appropriate sensors within the enclosure 202. In some implementations, the adhesive 204 should be thin enough to allow the sensors within the enclosure 202 to measure the physical parameters (e.g., secretions and other biometrics) from the user. For example, the adhesive 204 may have a thickness between about 0.001 inches to about 0.010 inches.

In some implementations, the enclosure 202 is sealed without openings or holes, such that it can prevent the entry of liquids into the internal compartment defined by the enclosure 202 in which the circuitry is housed. For instance, the enclosure 202 may be water-proof such that it can be used in wet environments including, e.g., the shower. The enclosure 202 may be constructed according to known standards for waterproofing, such as the International Electrotechnical Commission (IED) standard 60529 ingress protection (IP) code. For example, the enclosure 202 may be constructed such that water splashing against the enclosure 202 from any direction shall have no harmful effect, for example, water as applied from either: a) an oscillating fixture (when the enclosure 202 is subject to a minimum 10 minute test), or b) a spray nozzle with no shield (when the enclosure is subject to a minimum 5 minute test). Alternatively, or in addition, enclosure 202 may be configured to prevent ingress of water in harmful quantity (e.g., to damage the circuitry within the enclosure) when the enclosure 202 is immersed in water up to 1 meter of submersion for a minimum of 30 minutes. In such cases that the enclosure 202 is waterproof, the adhesive 204 also may be formed from a material that continues to adhere in wet conditions, such as solvent-based and low-temperature hot-melt adhesives.

The bone conduction device 200 may include one or more components 208, such as a transceiver and antenna, which allow the device 200 to send and receive wireless signals 212 from a remote device 210. The wireless signals 212 may carry information from the one or more sensors, such as the measurement signals generated by the one or more sensors, to the remote device 210. The wireless signals 212 may also carry information from the remote device 210, such as transducer control signals, back to the bone conduction device 200 responsive to the transmission of the measurement signals. The wireless signals may propagate according to one or more different wireless transmission protocols, such as low-power near field communication wireless protocols (e.g., Bluetooth, ZigBee, Z-Wave) and medium and long range wireless protocols (e.g., WiFi and cellular network protocols). The remote device 210 may include any device that is capable of communicating wirelessly with the bone conduction device 200 and that includes an electronic processor configured to process the received sensor signals and generate the transducer control signals. The remote device 210 may include a data processing apparatus, computer system or processor according to the present disclosure.

Figure 3:
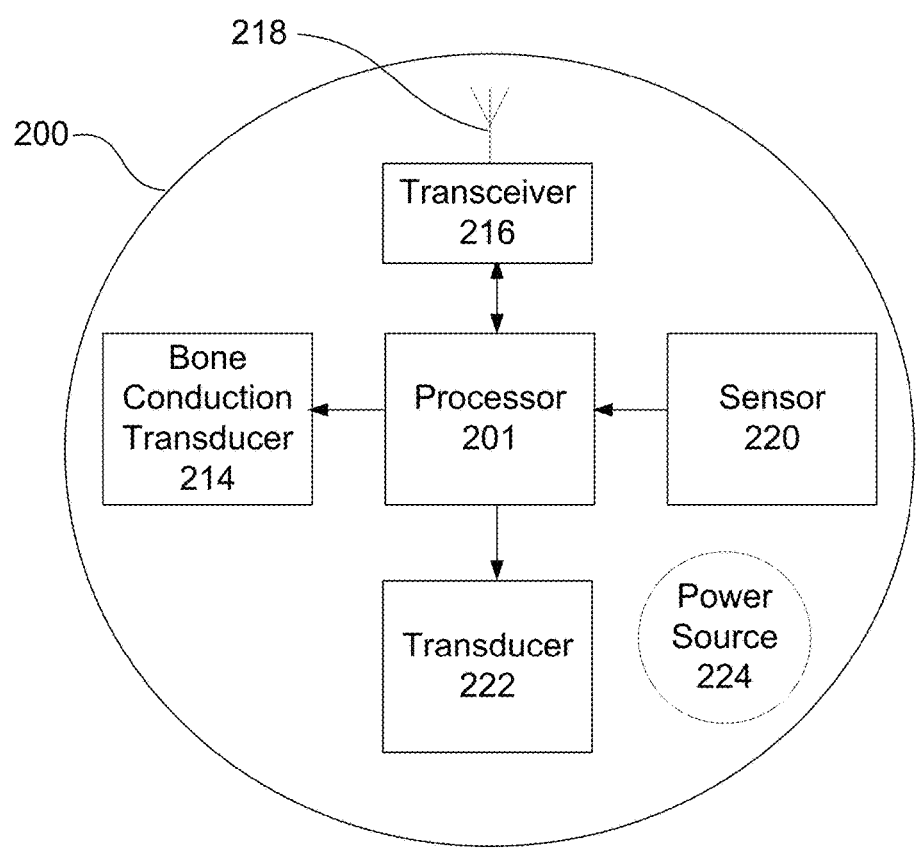
FIG. 3 is a schematic that illustrates an example of components that may be included within a bone conduction device according to the present disclosure.

FIG. 3 is a schematic that illustrates an example of the different components that may be included within the bone conduction device 200. For example, the device 200 may include an antenna 218 configured to transmit and receive wireless signals according to the wavelength appropriate to use with the selected wireless transmission protocol. In some implementations, the antenna 218 may be formed from an elongated strip of metal. For example, the antenna 218 may be in the shape of a coil. The device 200 further may include a transceiver 216 communicatively coupled to the antenna 218. The transceiver 216 may be configured to convert information received from one or more sensors 220 into a form suitable for transmission according to the selected transmission protocol, and to transmit the information through the antenna. The transceiver may be further configured to convert transducer control signals received by the antenna 218 into a form suitable for being used by the bone conduction transducer 214 and any other transducers 222 included within the enclosure of the device 200.

The device 200 further includes a bone conduction transducer 214 communicatively coupled to the transceiver 216. The bone conduction transducer 214 may include, e.g., a device capable of vibrating in response to receiving an electrical control signal. For instance, the bone conduction transducer 214 may include a piezoelectric crystal or other piezoelectric material capable of generating vibrations in the frequency range of about 100 Hz to about 10 KHz or higher. Other transducers capable of generating vibrations in response to an electrical control signal may be used instead. In some implementations, the bone conduction transducer is anchored to the enclosure 202 such that the vibration generated from the transducer 214 is transferred to the enclosure 202, and then from the enclosure 202 to the user when the device 200 is attached to the user. In some implementations, multiple bone conduction transducers 214 are included within the enclosure 202 to enhance the strength of the vibrations produced by the device 200. In such case, the bone conduction control signals are sent in phase from the transceiver to each one of the bone conduction transducers 214.

The device 200 further includes at least one sensor 220 communicatively coupled to the transceiver 216. As explained herein, the at least one sensor 220 may be configured to generate a measurement signal upon sensing a physical property associated with the user when the device 200 is attached to the user. The at least one sensor 220 may also be configured to transmit the measurement signal to the transceiver 216. For instance, the at least one sensor 220 may be configured, in some implementations, to generate a measurement signal indicative of non-audible physical property of the user such as: the user's pulse rate, the user's level of perspiration, the user's temperature, the user's acceleration, the user's velocity, the user's orientation, odors from the user, or other physical properties and biometrics of the user. In some implementations, the at least one sensor 220 includes a sensor, such as a microphone, configured to detect an audible output from the user. In some implementations, the at least one sensor 220 may be configured to generate a measurement signal upon sensing a physical property associated with the environment in which the user is located during operation of the device 200. For instance, the at least one sensor 220 may be configured to generate a signal indicative of the temperature of the ambient environment, sounds from the ambient environment, or chemicals (e.g., odors) from the ambient environment.

In some implementations, the device 200 may include circuitry, such as a local processor 201 (e.g., a local microprocessor), configured to modify the measurement signal or extract information from the measurement signal. For example, the at least one sensor 220 may include a microprocessor 201 configured to convert an analog measurement signal into a digital signal. In another example, the microprocessor 201 may be configured to extract frequency, phase and/or amplitude information from the measurement signal. In another example, the microprocessor may be configured to amplify a signal from the at least one sensor 220 before communicating the signal to the transceiver 216.

Examples of sensors that may be included in the device include microphone, accelerometer, speedometer, gyroscope, pressure sensor, pH sensor (e.g., fiber optic pH sensor or pH microelectrode), pulse sensor, pulse oximetry sensor, galvanometer, thermistors, glucose sensor, infrared sensors, visible light detectors, among others. One or more of the sensors may be fabricated as micro-electro mechanical systems (MEMS) and include corresponding circuitry for performing signal processing of the measured signals. One or more of the sensors may include a combination of a photodetector and light source, such as a light emitting diode (LED) or semiconductor laser source. Such sensors may be capable of directing light to the user's skin and measuring light reflectance to evaluate a bio-signature of the user (e.g., as in pulse oximetry). In an example use, the device 200 may include a galvanometer that generates a measurement signal in the form of electrical current upon detection of perspiration from a user.

In some implementations, the bone conduction transducer 214, the at least one sensor 220 and/or the transducer 222 is communicatively coupled to the microprocessor 201 and to the transceiver 216 through the microprocessor 201. In some implementations, the microprocessor 201 receives command signals from the transceiver 216 and redirects the command signals to the appropriate transducer in the device 200. In some implementations, the microprocessor 201 includes (either fabricated with the microprocessor or communicatively coupled to the microprocessor) a memory device (e.g., a flash memory or other semiconductor memory device) for storing data.

In some implementations, the device 200 includes at least one additional transducer 222. The additional transducer 222 also may be communicatively coupled to the transceiver 216 to receive a transducer control signal. The additional transducer 222 may be configured to generate an output that creates a physical sensation in the region of the user's skin to which the device 200 is attached for altering the user's perceived state or mood. For example, the additional transducer 222 may include a thermoelectric heater element that is capable of providing heat to the user, such as a resistive heating element or a Peltier heating element. In another example, the additional transducer 222 may include a thermoelectric cooling element, such as a Peltier cooler, that cools the region of the user's skin to which the device 200 is attached.

The device 200 further includes a power source 224. The power source 224 may be coupled to each of the transceiver 216, the at least one sensor 220, the bone conduction transducer 214, the microprocessor 201 and the at least one additional transducer 222. In some implementations, the power source 224 includes a battery, such as a lithium ion battery. In some implementations, the power source 224 may be rechargeable. For example, the power source 224 may include a battery that is coupled to a charging port on the enclosure 202, such as a universal serial bus (USB) or a micro-USB port. The battery then may be recharged by connecting the charging port to an external power supply through a cable adapted to couple to the charging port. In another example, the battery may be recharged though motion of the device 200. This type of recharging, also known as self-charging or "power through movement technology," transforms kinetic energy into power. Thus, when a user wearing the device 200 moves around (e.g., by walking, jumping or other movement that causes the device 200 to move as well), the battery will convert some of the kinetic energy of the user into power that is used to recharge itself. The self-charging battery may include a rotating pendulum, gear and micro-electrical generator configured in a similar manner as a self winding watch. Alternatively, or in addition, the self-charging battery may be based on electromagnetic induction. For example, the self-charging battery may include a moveable magnet within the enclosure that shifts position relative to a wire coil as a user moves with the device 200. The motion of the magnet past the coil may generate electrical current within the coil that can be used to recharge the battery. In some implementations, the antenna may also be used as the coil for recharging the battery.

In some implementations, the power source 224 may be recharged wirelessly. For instance, the power source 224 may include a battery that can be re-charged through resonant magnetic coupling. In an example, the device 200 may include a coil (which can double as the antenna 218) coupled to the battery that, when situated near an oscillating magnetic field emanating from a base power supply station, couples to the magnetic field at a resonance frequency. The resonance coupling may result in the generation of electrical current within the coil located in the device 200, where the newly generated electrical current may be used to recharge the battery. In the foregoing implementations, the recharging may be used to partially recharge the battery or completely recharge the battery depending, e.g., on the typical power consumption of device 200 and the power generated by the recharging mechanism.

In some implementations, the device 200 is configured to be disposable. That is, the device 200 may be designed for so-called "one-time use" by a user or may be configured to operate for a maximum period of time. For example, the power source 224 may include a non-rechargeable power supply provided with a fixed charge that would allow the device 200 to continuously operate for a maximum period of time such as, one day, two days, three days, one week, two weeks, or one month. Other time periods are possible as well. In some implementations, the disposable device 200 is configured such that the one or more of the sensors 220 continuously monitor some aspect of the user and/or of the environment during the fixed time period of operation. For example, a disposable device 200 may be configured to monitor a pulse rate in the user during a two-week operation lifetime of the device 200.

In some implementations, the device 200 is configured such that it can be automatically activated from a deactivated state upon a triggering event/signal. Automatic activation of the device 200 may be understood as, for example, providing power to the bone conduction transducer 214, the transceiver 216 and/or one or more of the sensors 220. For example, in some implementations, automatic activation includes providing power to the bone conduction transducer 214 such that the transducer 214 can receive bone control signals from the transceiver 216 and generate vibrations responsive to receiving the bone conduction signals. In this case, other components may be pre-activated prior to receiving the triggering signal. For example, other components may already be receiving a low level of power from the power source 224 to monitor for the triggering event/signal. Once the triggering event/signal is detected, commands and/or measurement signals may be sent to the processor 201, which in turn, allows power to be delivered to the bone conduction transducer 214. The triggering signal to initiate activation may be an activation command or control signal received wirelessly by the transceiver 216. Alternatively, or in addition, the triggering signal may be received through one or more of the sensors 220.

In another example, automatic activation includes providing power to the bone conduction transducer 214 as well as the transceiver 216 such that the transceiver 216 can receive control signals and send measurement signals from the sensors 220. In this example, one or more of the sensors 220 may be pre-activated prior to receiving the triggering signal/event. For instance, as explained above, the one or more sensors 220 may send a measurement signal to the processor 201 such that the processor 201 allows the bone conduction transducer 214 and transceiver 216 to receive power.

The triggering signal/event may include, in some implementations, a wireless command sent from the remote device 210 and received at the transceiver 216. The triggering signal/event may include, in some implementations, a change in ambient conditions measured by one or more of the sensors 220. For example, in some implementations, the deactivated device 200 may be contained within packaging for sale to an end-user. The environment within the package may be a low-pressure/vacuum environment. The device 200 may include a sensor (e.g., a pressure sensor) that is capable of detecting a change in air pressure within the ambient environment, such that once the package is opened and the device 200 is exposed to a higher pressure, a measurement signal is recorded by the sensor 220 and sent to the processor 201. The processor 201, in turn, issues a command to power the bone conduction transducer 214 and transceiver 216. Other types of ambient conditions that may be used as a triggering event including, for example, a change in temperature (e.g., an increase in temperature above a predetermined threshold temperature or a decrease in temperature below a predetermined threshold temperature), a change in sound (e.g., measurement of an increase in sound volume above a predetermined threshold volume, so that a person speaking into the device 200 may activate the device 200), a change in humidity (e.g., an increase in humidity above a predetermined threshold humidity or a decrease in humidity below a predetermined threshold humidity), a change in light intensity (e.g., an increase in the amount of visible light detected above a predetermined threshold value or a decrease in the amount of visible light detected below a predetermined threshold value.), or a change in motion (e.g., change in velocity and/or acceleration above or below a predetermined threshold) of the device 200 Other ambient conditions in combination with an appropriate sensor may be used as well to automatically activate the device.

In some implementations, the triggering event/signal is indicative of the device 200 having been adhered to the user's skin such that the device 200 may be activated when it is applied to the user, but not before then. For example, one or more sensors 220 in the device 200 may be configured to detect perspiration such that when the device 200 is placed against the user's skin and perspiration is detected, a measurement signal is generated by the perspiration sensor and passed to the processor 201, which, in turn, issues a command to power the bone conduction transducer 214 and/or transceiver 216. In another example, one or more sensors 220 in the device 200 may be configured to detect a user's pulse. Thus, when the device 200 is placed against a user's skin and a pulse is detected, a measurement signal is generated from the pulse sensor and passed to processor 201, which, in turn, issues a command to power the bone conduction transducer 214 and/or transceiver 216.

In some implementations, the device 200 may be configured such that it deactivates when removed from a user's skin. Using the above example of the perspiration detector, a measurement signal may be generated when a threshold level of perspiration is no longer detected. This measurement signal then may be passed to the microprocessor 201, which, in turn, issues a command to remove power from the bone conduction transducer 214, the transceiver 216 or other component of the device 200. In another example, a measurement signal may be generated when a pulse is no longer detected by a pulse detector. This measurement signal then may be passed to the microprocessor 201, which, in turn, issues a command to remove power from the bone conduction transducer 214, the transceiver 216 or other component of the device 200.

In some implementations, the device 200 is configured such that it may authenticate the user to which the device 200 is adhered. For example, the microprocessor 201 may be configured to record and save to memory biometric measurement signals that are unique to a user. The biometric measurement signals may be obtained from the one or more sensors 220 in the device 200. The saved biometric signals may be compared against new measurement signals from the same sensors 220 at a later time to determine whether there is a match. Upon identifying a match, the microprocessor 201 may authenticate the user. For instance, the biometric signals that are used for authentication may include pulse rate, voice, perspiration (e.g., chemical and/or ionic levels within the perspiration), or the user's particular gait (e.g., based on the uniqueness of the user's velocity, acceleration and/or orientation), among others. In each case, the microprocessor 201 may be configured to identify unique patterns within the measurement signals that are associated with a particular user. In an example, the device 200 may include a microphone that is capable of recording the user's voice. The microprocessor 201 may be configured to perform voice recognition on the recorded voice and identify whether the recorded voice belongs to a particular user. In some implementations, multiple biometric measurement signals, each of which is unique to a different user, are saved by the microprocessor 201 and memory, such that the device 200 may authenticate more than one user. In some implementations, the authentication process may occur periodically, such that the device 200 repeatedly confirms the user to which the device 200 is attached. For example, the device 200 may perform an authentication process every minute, every ten minutes, every hour, every five hours, every day, among other periods.

In some implementations, the device 200 may use the foregoing authentication capability to activate or deactivate the device 200. For example, when the device 200 is adhered to a user's skin, the device 200 may be configured to authenticate the user based on the user's unique biometric signature as explained above. Upon recognition of the user's unique biometric signature, the device 200 may activate the bone conduction transducer 214 and/or other components within the device 200. Upon removing the device 200 from the user, however, the device 200 may recognize removal through the loss of the biometric signature and subsequently deactivate the bone conduction transducer 214 and/or other components within the device 200. In some implementations, the device 200 may be attached to a user for which the device 200 is unable to authenticate (e.g., biometric signatures unique to the user have not been stored in the device 200). In such cases, the device 200 will not activate one or more components (e.g., bone conduction transducer 214 or transceiver 216) within the device 200.

Figure 4:
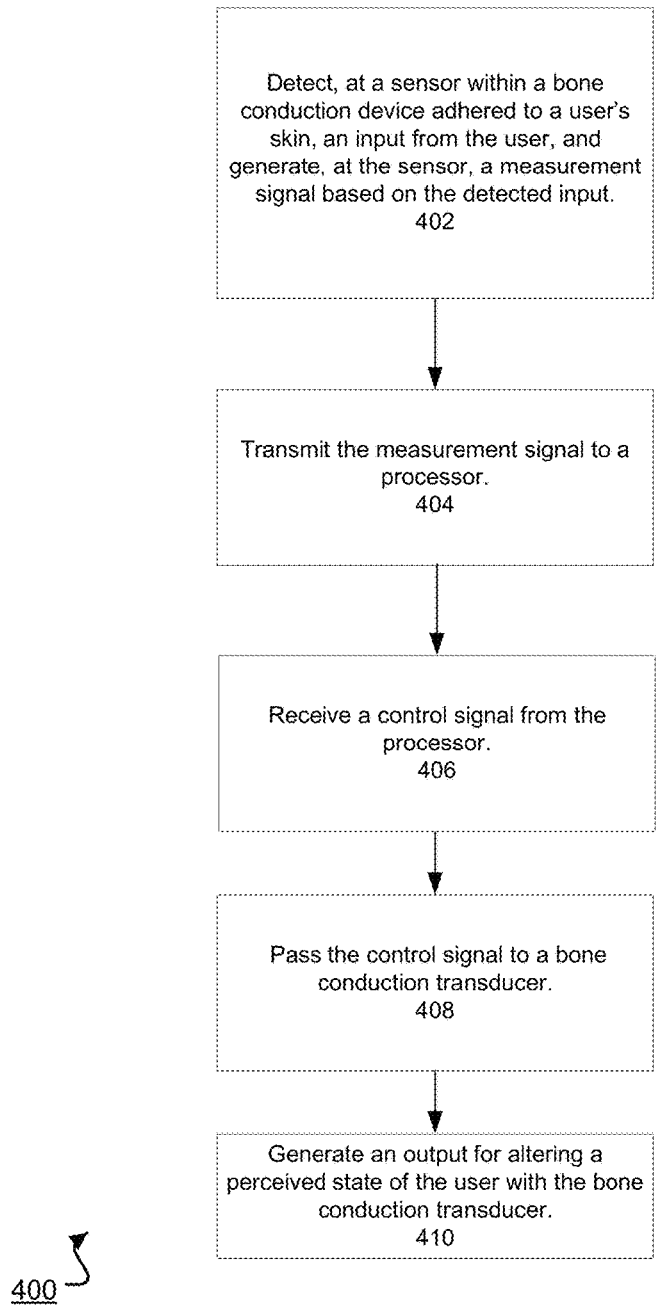
FIG. 4 is a schematic that illustrates an example process 400 performed by a bone conduction device.

FIG. 4 is a schematic that illustrates an example process 400 of using a bone conduction device, such as any of the implementations described herein. In a first step (402), a sensor (e.g., sensor 220) within the bone conduction device, detects an input from a region of skin to which the bone conduction device is adhered and generates a measurement signal based on the detected input. The at least one sensor may be configured to detect a non-audible input from the region of the user's body to which the bone conduction device adheres. The at least one sensor may be configured to detect an input from the ambient environment in which the user and/or bone conduction device is located. The one or more measurement signals may correspond to biometric signals from the user and/or may correspond to signals representative of a condition of the ambient environment. In some implementations, the bone conduction device receives multiple different measurement signals from multiple sensors within the bone conduction device, including, e.g., at least one measurement signal based on a non-audible input to a sensor and at least one measurement signal based on an audible input to another sensor.

In a second step (404), the bone conduction device transmits (e.g., using transceiver 216) the measurement signal to a processor for analysis. In some implementations, the measurement signal may be pre-processed before transmission. For example, the measurement signal may be converted to digital signals and/or to signals compatible with a transmission protocol. In some implementations, the processor receiving the signal is located within a device that is remote from the bone conduction device. The processor receiving the measurement signals may analyze the measurement signals. Based on the analysis, the processor may generate one or more control signals. The one or more control signals may include control signals for the bone conduction transducer (e.g., transducer 214) or other transducers included in the bone conduction device. The one or more control signals may be configured such that, when applied by the appropriate transducer, they may cause the transducer to create an output that alters a perceived state, emotion and/or experience of a user. The processor may pass the control signals to the transducers in the bone conduction device. For example, if the processor is located in a remote device, the remote device may wirelessly transmit the control signals to the bone conduction device.

In a third step (406), the bone conduction device receives the control signals. For example, the transceiver 416 may receive wireless communications from the remote device, in which the wireless communications include the control signals.

In a fourth step (408), the control signals are passed to the appropriate transducers within the bone conduction device. For example, bone conduction control signals are sent to the bone conduction transducer, whereas a heating element or cooling element control signal is sent to a heating device or cooling device, respectively.

In a fifth step (410), the transducers receiving the control signals generate an output for altering a perceived state, emotion and/or experience of a user based on the received control signals. For example, the bone conduction transducer may generate vibrations that are capable of passing through the user's skull to the user's auditory system so that the user can hear a particular sound, or may generate other output as described herein.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the processor 201 and processor in the remote device 210 can be implemented using digital electronic circuitry, or in computer software, firmware, or hardware, or in combinations of one or more of them. In another example, processes depicted in FIG. 4 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computing system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. For example, the actions recited in the claims can be performed in a different order and still achieve desirable results. In certain circumstances, multitasking and parallel processing may be advantageous. Moreover, the separation of various components in the implementations described above should not be understood as requiring such separation in all implementations.

A number of aspects, implementations, and embodiments have been described. Nevertheless, it will be understood that various modifications may be made without departing from the spirit and scope of the invention. Accordingly, other aspects, implementations, and embodiments are within the scope of the following claims.

What is claimed is:

1. A bone conduction device comprising:
an enclosure; and
an adhesive applied to a surface of the enclosure, the adhesive being configured to be removably adhered to a user's skin,
wherein the enclosure comprises:
a bone conduction transducer configured to cause the enclosure to vibrate in response to receiving a bone-conduction control signal;
at least one sensor configured to, during operation of the bone conduction device, sense a non-audible input from a region of the user's skin to which the adhesive adheres and produce a sensor output signal in response to sensing the non-audible input, the sensor output signal being indicative of a current state of the user; and
a transceiver coupled to the bone conduction transducer and to the at least one sensor, wherein the transceiver is configured to a) receive the output signal from the at least one sensor and transmit the output signal to a remote processor and b) in response to transmitting the output signal, receive the bone-conduction control signal from the remote processor and transmit the bone-conduction control signal to the bone conduction transducer,
wherein the bone conduction device is configured to be activated upon the bone conduction device being exposed to a triggering event,
wherein the triggering event is indicative of the bone conduction device having been applied to the user's skin,
wherein the bone conduction device is configured to deactivate upon being removed from the user's skin,
wherein the adhesive is thin enough to allow secretions from the user to enter into openings within the enclosure, and wherein the at least one sensor, the bone conduction transducer and the transceiver are positioned on a flexible board within the enclosure.

2. The bone conduction device of claim 1, wherein the at least one sensor comprises one or more of an accelerometer, a speedometer, a gyroscope, a galvanometer, a photodetector, a temperature sensor, a pulse oximetry sensor, a glucose monitor, and a pressure sensor.

3. The bone conduction device of claim 1, further comprising an additional transducer, the additional transducer being configured to generate a non-audible sensation and direct the non-audible sensation to the region of the user's skin to which the adhesive adheres.

4. The bone conduction device of claim 3, wherein the additional transducer comprises a heating device or a cooling device.

5. The bone conduction device of claim 1, wherein the triggering event comprises an activation control signal.

6. The bone conduction device of claim 1, wherein the bone conduction device is configured to authenticate the user upon being adhered to the user's skin.

7. The bone conduction device of claim 6, wherein the bone conduction device is configured to authenticate the user based on an analysis of a biometric measurement signal generated by the at least one sensor.

8. The bone conduction device of claim 7, comprising a local processor communicatively coupled to the at least one sensor and configured to receive and analyze the biometric measurement signal generated by the at least one sensor.

9. The bone conduction device of claim 7, wherein the bone conduction device comprises a local processor communicatively coupled to the at least one sensor, wherein the local processor is configured to perform authentication upon being adhered to the user's skin.

10. The bone conduction device of claim 1, wherein the bone conduction device is configured to authenticate a plurality of users based on a plurality of biometric measurement signals, each biometric measurement signal of the plurality of biometric measurement signals being unique to a different respective user of the plurality of users.

11. The bone conduction device of claim 1, wherein the enclosure is flexible such that it is capable of conforming to a shape of the user's body upon being adhered to the user's skin.

12. The bone conduction device of claim 1, wherein the adhesive is an acrylic-based pressure sensitive adhesive.

13. The bone conduction device of claim 1, wherein the bone-conduction control signal is configured to cause the bone conduction transducer to generate an output to alter the state of the user or the user's perception of the state.

14. A bone conduction device comprising:
an enclosure; and
an adhesive applied to a surface of the enclosure, the adhesive being configured to be removably adhered to a user's skin,
wherein the enclosure comprises:
a bone conduction transducer configured to cause the enclosure to vibrate in response to receiving a bone-conduction control signal;
at least one sensor configured to, during operation of the bone conduction device, sense a non-audible input from a region of the user's skin to which the adhesive adheres and produce a sensor output signal in response to sensing the non-audible input, the sensor output signal being indicative of a current state of the user; and
a transceiver coupled to the bone conduction transducer and to the at least one sensor, wherein the transceiver is configured to a) receive the output signal from the at least one sensor and transmit the output signal to a remote processor and b) in response to transmitting the output signal, receive the bone-conduction control signal from the remote processor and transmit the bone-conduction control signal to the bone conduction transducer,
wherein the bone conduction device is configured to record a biometric signal unique to the user and is configured to activate one or more components of the bone conduction device upon a subsequent detection and recognition of the unique biometric signal,
wherein the adhesive is thin enough to allow secretions from the user to enter into openings within the enclosure, and wherein the at least one sensor, the bone conduction transducer and the transceiver are positioned on a flexible board within the enclosure.

15. The bone conduction device of claim 14, wherein the biometric signal comprises a signal indicative of the user's pulse rate, the user's voice, the user's perspiration, or the user's gait.

* * * * *